United States Patent [19]

Schaumann et al.

[11] 4,436,735
[45] Mar. 13, 1984

[54] KETALS OF 3'''-DEHYDROCARDENOLIDE TRIDIGITOXOSIDES

[75] Inventors: Wolfgang Schaumann, Heidelberg; Fritz Kaiser, Lampertheim; Wolfgang Voigtländer, Weinheim; Edgar Hoyer, Mannheim; Peter Neubert, Weinheim, all of Fed. Rep. of Germany

[73] Assignee: Boehringer Mannheim GmbH, Mannheim, Fed. Rep. of Germany

[21] Appl. No.: 439,653

[22] Filed: Nov. 5, 1982

[30] Foreign Application Priority Data

Nov. 26, 1981 [DE] Fed. Rep. of Germany ....... 3146899

[51] Int. Cl.³ .................. A61K 31/585; C07J 19/00
[52] U.S. Cl. ..................................... 424/182; 536/61
[58] Field of Search ......................... 536/6.1; 424/182

[56] References Cited

U.S. PATENT DOCUMENTS 3,907,775 9/1975 Lösel et al. ..................... 536/6.1
3,909,357 9/1975 Reinhard et al. ................ 536/6.1

Primary Examiner—Johnnie R. Brown
Assistant Examiner—Elli Peselev
Attorney, Agent, or Firm—Felfe & Lynch

[57] ABSTRACT

The present invention provides ketals of 3'''-dehydrocardenolide tridigitoxosides of the general formula:

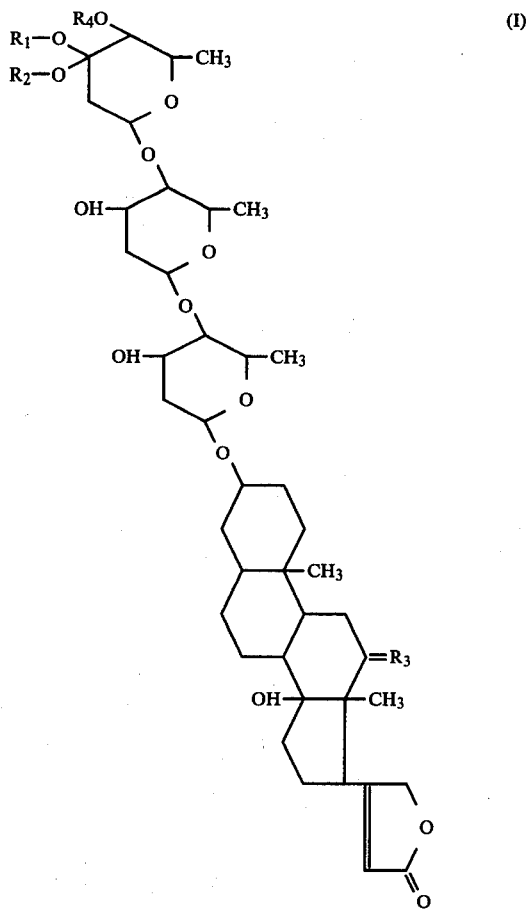

in which $R_1$ and $R_2$ are identical alkyl radicals containing up to 3 carbon atoms or together represent a cyclic ketal containing 2 to 6 carbon atoms, $R_3$ represents two hydrogen atoms, the group

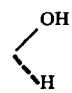

or the radical

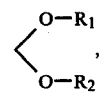

wherein $R_1$ and $R_2$ have the above-given meaning, and $R_4$ is a hydrogen atom or a lower acyl or alkyl radical.

The present invention also provides processes for the preparation of these ketals, as well as pharmaceutical compositions containing them, which are useful for the treatment of cardiac insufficiency.

20 Claims, No Drawings

KETALS OF 3'''-DEHYDROCARDENOLIDE TRIDIGITOXOSIDES

The present invention is concerned with new ketals of 3'''-dehydrocardenolide tridigitoxosides, processes for the preparation thereof and pharmaceutical compositions containing them which are useful for the treatment of cardiac insufficiency.

The new ketals according to the present invention are compounds of the general formula:

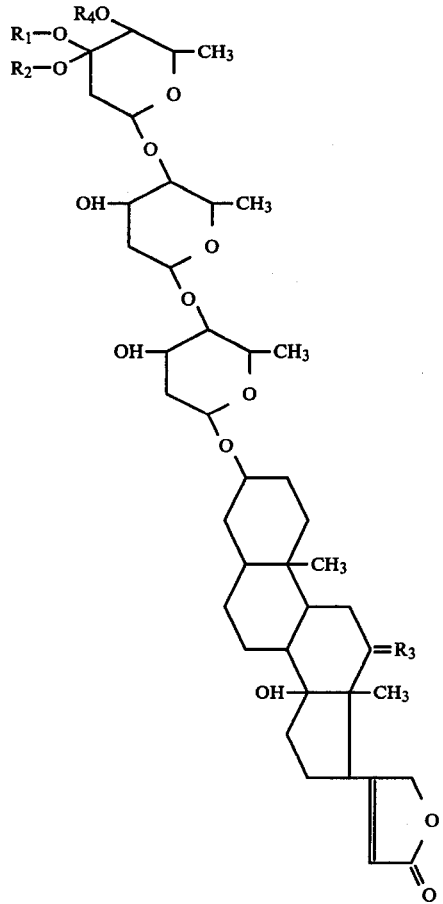

in which $R_1$ and $R_2$ are identical alkyl radicals containing up to 3 carbon atoms or together represent a cyclic ketal containing 2 to 6 carbon atoms, $R_3$ represents two hydrogen atoms, the group

or the radical

wherein $R_1$ and $R_2$ have the above-given meanings, and $R_4$ is a hydrogen atom or a lower acyl or alkyl radical.

Acyl radicals are to be understood to be alkanoyl radicals containing up to 3 carbon atoms, the acetyl radical being preferred, and alkyl radicals are to be understood to be those containing up to 3 carbon atoms, the methyl radical being preferred.

The Digitalis glycosides digitoxin and digoxin mainly used in the therapy of heart insufficiency, as well as their derivatives, for example acetyldigoxin and methyldigoxin, still leave something to be desired for the safety of their use: digoxin and its derivatives are preponderantly eliminated through the kidneys and can, therefore, lead to intoxications in the case of patients with impaired kidney function. Digitoxin is the glycoside with the longest period of residence in the organism, for which reason possibly occurring intoxications, for example in the case of overdosing, can only subside again extremely slowly.

We have now found that the ketals of 3'''-dehydrocardenolide tridigitoxosides according to the present invention occupy an ideal middle position in that they are preponderantly eliminated extrarenally and thus, in the case of impaired kidney function, are less dangerous and, in addition, they are eliminated considerably more quickly than digitoxin, with elimination times being similar to that of digoxin.

The new compounds of general formula (I) can be prepared by reacting a compound of the general formula:

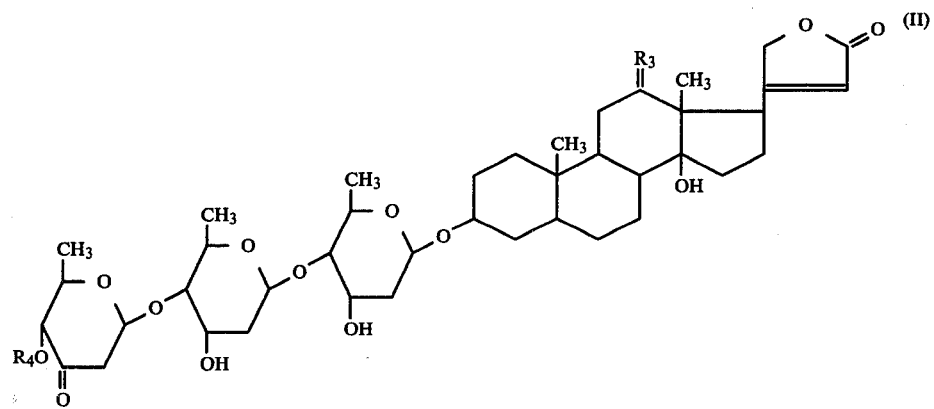

in which $R_4$ is hydrogen or a lower alkyl radical and $R_3$ represents two hydrogen atoms, the group

or an oxygen atom, in per se known manner with a monohydroxy alkanol containing up to 3 carbon atoms or with a dihydroxy alkanol containing 2 to 6 carbon atoms, to give a ketal.

The reaction is usually carried out in the alkanol in question as solvent, with the addition of an acidic catalyst at a temperature of from ambient temperature to the boiling point of the solvent. The reaction is promoted by a water-binding agent, preferably an orthoformic acid ester, or by a non-polar solvent which distills off azeotropically with water, for example benzene or toluene.

The working up of the reaction mixture and purification of the end products takes place according to usual methods, including the use of chromatographic processes or by multiplicative partitioning and crystallization.

The identity and purity of the compounds obtained were tested by thin layer chromatograms, using TLC finished plates (Merck silica gel 60/F 254, impregnation 20% formamide in acetone) and developing with the elution agent heptane-methyl ethyl ketone (1:1 v/v)+1.8% formamide or the elution agent xylene-methyl ethyl ketone (2:3 v/v)+5% formamide in Example 6. The finished chromatograms were sprayed with trichloroacetic acid-chloramine reagent and the substances determined by their fluorescence in long-wave UV ($\lambda = 360$ nm). The running paths (R) in the chromatogram were, in each case, referred to a simultaneously run standard. $R_{Dt}$ thereby signifies the R value referred to the running path of 3′″-dehydrodigitoxin, $R_D$ and R value referred to the running path of 3′″,12-didehydrodigoxin and $R_{Dg}$ the R value referred to the running path of 3′″-dehydrodigoxin.

The cardenolide glycosides according to the present invention can be administered 1 to 4 times daily in individual dosings of 0.05–1.0 mg. Administration is preferably orally but a parenteral administration can also be used.

The oral forms of administration are preferably tablets but hard capsules and soft gelatine capsules can also be used. For individual cases, for example for children, the preparation can be in the form of a liquid. For emergency and stationary treatment, administration can be by injection of appropriate solutions.

For the preparation of the tablets or hard capsules for oral administration, the active material is mixed with conventional adjuvants, such as lactose and starch, whereby, because of the small individual dose, the production of a pre-mixture is preferred. The active material-adjuvant mixture can be filled into hard capsules as a dry powder mass or, by granulation with binding agents, such as starch slurry or polyvinylpyrrolidone, as granulate or, after further admixture of conventional breakdown agents and lubricants, pressed into tablets.

Carrier materials for soft gelatine capsules can be the usual glycerol fatty acid esters but polyethyleneglycols can also be used as solvent for the active material. For a liquid or ampoule form, as solvent there can be used ethanol or polyhydroxy alcohols, optionally with the addition of water and other conventional adjuvants.

The advantages of the compounds according to the present invention in comparison with digoxin and digitoxin, i.e. the compounds have a more rapid elimination with an increased rate of elimination via bile/feces, is shown by the following experimental protocol:

EXPERIMENTAL PROTOCOL

Groups of 4 cats each received an intravenous dose of 20 μg./kg. of one of the glycosides mentioned in the following Table. The glycosides were marked with tritium by the method of Haberland and Maerten* and the digoxin was marked with tritium by the method of Wartburg.**

*German Published Specification No. 19 59 064
*Biochem. Pharmacol. 14, 1883 (1965)

The radioactivity was determined in the separately collected urine and fecal portions after 2 and 7 days.

The values summarised in the Table give the rate of elimination (column I) and the proportion of the elimination in the urine (column II).

Column I gives the amount eliminated in the urine+feces after 2 days as a percentage of the total elimination after 7 days Column II gives the percentage proportion of the elimination in the urine after 7 days, referred to the total elimination in urine+feces after 7 days.

| glycoside | I | II |
|---|---|---|
| digoxin | 53 | 44 |
| digitoxin | 20 | 16 |
| 3′″-dehydrodigitoxin dimethylketal | 48 | 27 |
| 3′″-dehydrodigitoxin ethyleneketal | 43 | 24 |

The following Examples are given for the purpose of illustrating the present invention:

EXAMPLE 1

3′″-Dehydrodigitoxin dimethylketal 2 g. 3′″-Dehydrodigitoxin are dissolved in 40 ml. anhydrous methylene chloride and 40 ml. methanol and, after the addition of 10 ml. triethyl orthoformate and 50 mg. p-toluenesulphonic acid, the reaction mixture is left to stand for 1 day at ambient temperature, then diluted with 80 ml. 5% aqueous sodium bicarbonate solution, shaken out with chloroform and the chloroform phases are washed with water and evaporated in a vacuum. The crude product is separated with cyclohexane-ethyl acetate (2:1 v/v) over a cellulose column impregnated with formamide. The chromatographically uniform fractions give, after crystallisation from acetone, 640 mg. 3′″-dehydrodigitoxin dimethylketal; m.p. 206°–210° C.; $R_{Dt}$: 1.96.

EXAMPLE 2

3′″-Dehydrodigitoxin diethylketal 2 g. 3′″-Dehydrodigitoxin are dissolved in 40 ml. methylene chloride and 40 ml. absolute ethanol, mixed with 10 ml. triethyl orthoformate and 50 mg. p-toluenesulphonic acid, left to stand for 2 days at ambient temperature and worked up as described in Example 1. The crude product is separated with heptane-methyl ethyl ketone (5:1 v/v) over a cellulose column impregnated with formamide. The chromatographically uniform fractions give, after crystallisation from acetone, 720 mg. 3′″-dehydrodigitoxin diethylketal; m.p. 189°–193° C.; $R_{Dt}$: 2.89.

EXAMPLE 3

3'''-Dehydrodigitoxin ethyleneketal 2 g. 3'''-Dehydrodigitoxin are dissolved in 40 ml. methylene chloride and 40 ml. ethylene glycol and, after the addition of 10 ml. triethyl orthoformate and 50 mg. p-toluenesulphonic acid, are reacted and worked up as described in Example 2. The crude product is fractionated with carbon tetrachloride-ethyl acetate (3:7 v/v+2% water) over silica gel (+2% water). The chromatographically uniform fractions yield, after crystallisation from acetone, 550 mg. 3'''-dehydrodigitoxin ethyleneketal; m.p. 152°–156° C.; $R_{Dt}$: 1.26.

EXAMPLE 4

3'''-Dehydrodigitoxin propyleneketal 2 g. 3'''-Dehydrodigitoxin are dissolved in 40 ml. methylene chloride and 40 ml. propane-1,2-diol and mixed with 10 ml. triethyl orthoformate and 50 mg. p-toluenesulphonic acid and reacted and worked up as described in Example 2. The crude product is separated with cyclohexane-ethyl acetate (2:1 v/v) over a cellulose column impregnated with formamide. The chromatographically uniform fractions give, after crystallisation from acetone, 630 mg. 3'''-dehydrodigitoxin propyleneketal; m.p. 159°–163° C.; $R_{Dt}$: 1.68.

EXAMPLE 5

3''',12-Didehydrodigoxin bis-(diethylketal)

2 g. 3''',12-Didehydrodigoxin are dissolved in 40 ml. absolute ethanol and 40 ml. methylene chloride and, after the addition of 10 ml. triethyl orthoformate and 50 mg. p-toluenesulphonic acid, are left to stand for 1 day at ambient temperature. The reaction mixture is diluted with 80 ml. 5% aqueous sodium bicarbonate solution, shaken out with 6×30 ml. chloroform and the chloroform phases are washed with water and evaporated in a vacuum. The crude product is chromatographed over silica gel with cyclohexane and increasing amounts of ethyl acetate. Chromatographically uniform fractions give, after crystallisation from acetone, 0.6 g. 3''',12-didehydrodigoxin bis-(diethylketal); m.p. 190°–195° C.; $R_D$: 6.0.

EXAMPLE 6

3'''-Dehydrodigoxin dimethylketal 1 g. 3'''-Dehydrodigoxin is dissolved in 20 ml. anhydrous methylene chloride and 20 ml. methanol and, after the addition of 5 ml. triethyl orthoformate and 25 mg. p-toluenesulphonic acid, is reacted and worked up as described in Example 1. The crude product is separated with xylene-methyl ethyl ketone (3:1 v/v) over a cellulose column impregnated with formamide. The chromatographically uniform fractions yield, after crystallisation from acetone-diethyl ether-petroleum ether, 410 mg. 3'''-dehydrodigoxin dimethylketal; m.p. 131°–135° C.; $R_{Dg}$: 1.67.

EXAMPLE 7

4'''-Acetyl-3'''-dehydrodigitoxin ethyleneketal 1 g. 3'''-Dehydrodigitoxin ethyleneketal is dissolved in 10 ml. dimethylformamide and, after the addition of 230 mg. triethylenediamine and 0.20 ml. acetic anhydride, left to stand for 24 hours at ambient temperature. The reaction mixture is then diluted with 80 ml. water, shaken out with chloroform and the chloroform phases are evaporated in a vacuum. The crude product is separated with heptane-methyl ethyl ketone (3:1 v/v) over a cellulose column impregnated with formamide. The chromatographically uniform fractions give, after crystallisation from acetone-diethyl ether, 510 mg. 4'''-acetyl-3'''-dehydrodigitoxin ethyleneketal; m.p. 239°–243° C.; $R_{Dt}$: 2.68.

EXAMPLE 8

4'''-Methyl-3'''-dehydrodigitoxin diethylketal 1 g. 4'''-Methyl-3'''-dehydrodigitoxin is dissolved in 20 ml. methylene chloride and 20 ml. absolute ethanol, mixed with 5 ml. triethyl orthoformate and 25 mg. p-toluenesulphonic acid, left to stand for 2 days at ambient temperature and worked up as described in Example 1. The crude product is separated with heptane-methyl ethyl ketone (4:1 v/v) over a cellulose column impregnated with formamide. The chromatographically uniform fractions yield, after crystallisation from diethyl ether-petroleum ether, 320 mg. 4'''-methyl-3'''-dehydrodigitoxin diethylketal; m.p. 226°–230° C.; $R_{Dt}$: 4.68.

The 4'''-methyl-3'''-dehydrodigitoxin used as starting material is new and is prepared as follows:

6 g. Chromium trioxide are introduced at ambient temperature, while stirring, into a mixture of 8 ml. pyridine and 150 ml. methylene chloride and the mixture is stirred for 15 minutes at ambient temperature. A solution of 8 g. 4'''-methyldigitoxin in 10 ml. pyridine and 100 ml. methylene chloride is slowly added thereto, the reaction mixture is stirred for 15 minutes at ambient temperature, then heated to the boil under reflux for 1 hour, diluted with 500 ml. water, shaken out with chloroform and the chloroform phases are washed with a 5% aqueous solution of sodium bicarbonate and water, dried over anhydrous sodium sulphate and evaporated in a vacuum. The crude product is separated with heptane-methyl ethyl ketone (2:1 v/v) over a cellulose column impregnated with formamide. The chromatographically uniform fractions yield, after crystallisation from chloroform-diethyl ether, 4.2 g. 4'''-methyl-3'''-dehydrodigitoxin; m.p. 213°–217° C.

It will be understood that the specification and examples are illustrative but not limitative of the present invention and that other embodiments within the spirit and scope of the invention will suggest themselves to those skilled in the art.

What is claimed is:

1. A ketal of 3'''-dehydrocardenolide tridigitoxosides of the general formula:

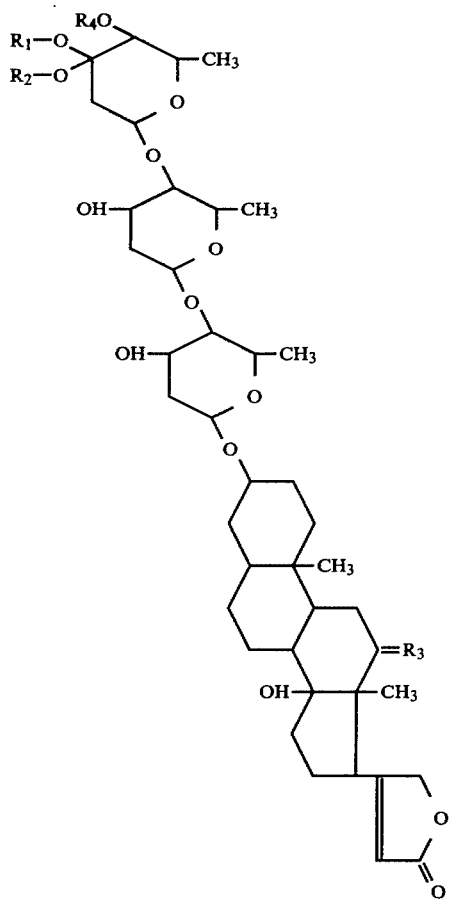

in which $R_1$ and $R_2$ are identical alkyl radicals containing up to 3 carbon atoms or together represent a cyclic ketal containing 2 to 6 carbon atoms, $R_3$ represents two hydrogen atoms, the group

or the radical

  (I)

wherein $R_1$ and $R_2$ have the above-given meaning, and $R_4$ is a hydrogen atom or a lower acyl or alkyl radical with up to 3 carbon atoms.

2. The ketal of claim 1 wherein $R_4$ is acetyl.
3. The ketal of claim 1 wherein $R_4$ is methyl.
4. The ketal of claim 1 wherein $R_4$ is hydrogen.
5. The ketal of claim 1 wherein $R_4$ is a lower acyl up to 3 carbon atoms.
6. The ketal of claim 1 wherein $R_4$ is an alkyl of up to 3 carbon atoms.
7. The ketal of claim 1 wherein $R_3$ is two hydrogen atoms.
8. The ketal of claim 1 wherein $R_3$ is

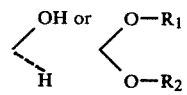

9. The ketal of claim 1 wherein $R_1$ and $R_2$ together represent a cyclic ketal containing 2 to 6 carbon atoms.
10. The ketal of claim 1 wherein $R_1$ and $R_2$ are identical alkyl radicals containing up to 3 carbon atoms.
11. The ketal of claim 1 which is designated 3'''-dehydrodigitoxin dimethylketal.
12. The ketal of claim 1 which is designated 3'''-dehydrodigitoxin diethylketal.
13. The ketal of claim 1 which is designated 3'''-dehydrodigitoxin ethyleneketal.
14. The ketal of claim 1 which is designated 3'''-dehydrodigitoxin propyleneketal.
15. The ketal of claim 1 which is designated 3''',12-didehydrodigoxin bis-(diethylketal).
16. The ketal of claim 1 which is designated 3''' dehydrodigoxin dimethylketal.
17. The ketal of claim 1 which is designated 4'''-acetyl-3'''-dehydrodigitoxin ethyleneketal.
18. The ketal of claim 1 which is designated 4'''-methyl-3'''-dehydrodigitoxin diethylketal.
19. Pharmaceutical composition for the treatment of cardiac insufficiency containing an effective amount of at least one ketal according to claim 1, in admixture with a pharmaceutical diluent or carrier.
20. A method of treating a cardiac insufficiency in a patient which comprise administering to such patient a cardioactive effective amount of a compound according to claim 1.

* * * * *